United States Patent
Mori

(10) Patent No.: US 9,050,045 B2
(45) Date of Patent: Jun. 9, 2015

(54) PSYCHOLOGICAL STATE ESTIMATION DEVICE

(75) Inventor: Hiroki Mori, Susono (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 551 days.

(21) Appl. No.: 12/525,466

(22) PCT Filed: Mar. 5, 2008

(86) PCT No.: PCT/JP2008/054429
§ 371 (c)(1),
(2), (4) Date: Jul. 31, 2009

(87) PCT Pub. No.: WO2008/108495
PCT Pub. Date: Sep. 12, 2008

(65) Prior Publication Data
US 2010/0009326 A1    Jan. 14, 2010

(30) Foreign Application Priority Data

Mar. 6, 2007  (JP) .................................. 2007-056235

(51) Int. Cl.
| | |
|---|---|
| G09B 19/00 | (2006.01) |
| A61B 5/00 | (2006.01) |
| A61B 5/16 | (2006.01) |
| A61B 5/18 | (2006.01) |

(Continued)

(52) U.S. Cl.
CPC .................. *A61B 5/18* (2013.01); *A61B 5/0205* (2013.01); *A61B 5/021* (2013.01); *A61B 5/024* (2013.01); *A61B 5/165* (2013.01); *A61B 5/441* (2013.01)

(58) Field of Classification Search
USPC ......................................................... 434/236
See application file for complete search history.

(56) References Cited

U.S. PATENT DOCUMENTS

| | | | |
|---|---|---|---|
| 6,870,478 B2 | 3/2005 | Yasushi et al. | |
| 2003/0097047 A1* | 5/2003 | Woltermann et al. | 600/300 |

(Continued)

FOREIGN PATENT DOCUMENTS

| | | |
|---|---|---|
| JP | A-8-140949 | 6/1996 |
| JP | A-2003-061939 | 3/2003 |

(Continued)

OTHER PUBLICATIONS

Japanese Office Action in Japanese Patent Application No. 2007-056235; dated Feb. 22, 2011 (w/ partial English-language translation).

(Continued)

*Primary Examiner* — Sam Yao
*Assistant Examiner* — James Hull
(74) *Attorney, Agent, or Firm* — Oliff PLC

(57) ABSTRACT

Disclosed is a psychological state estimation device for estimating the psychological state of a subject. A psychological state estimation device for estimating the psychological state of a subject includes bioinformation acquiring means for acquiring bioinformation of the subject, perception response acquiring means for acquiring the perception response of the subject to an external event, influence degree acquiring means for acquiring the degree of influence on a change in the psychological state of the subject on the basis of the acquired perception response, and estimating means for estimating the psychological state of the subject on the basis of the bioinformation and the degree of influence on the change in the psychological state.

2 Claims, 13 Drawing Sheets

(51) Int. Cl.
*A61B 5/0205* (2006.01)
*A61B 5/021* (2006.01)
*A61B 5/024* (2006.01)

(56) References Cited

U.S. PATENT DOCUMENTS

2003/0146841 A1* 8/2003 Koenig .......... 340/576
2004/0044293 A1* 3/2004 Burton .......... 600/544
2005/0075532 A1 4/2005 Lee et al.
2006/0025698 A1 2/2006 Nakagawa et al.
2006/0094934 A1* 5/2006 Shirai et al. .......... 600/300

FOREIGN PATENT DOCUMENTS

| JP | A-2004-024879 | 1/2004 |
| JP | A-2005-006966 | 1/2005 |
| JP | A-2005-157662 | 6/2005 |
| JP | A-2006-034803 | 2/2006 |
| JP | A-2006-167425 | 6/2006 |
| JP | A-2007-133673 | 5/2007 |

OTHER PUBLICATIONS

Japanese Office Action in Japanese Patent Application No. 2007-056235; dated Nov. 24, 2010 (w/ partial English-language translation).

International Preliminary Report on Patentability mailed Oct. 8, 2009 in International Application No. PCT/JP2008/054429.

* cited by examiner

Fig.6

| ENVIRONMENTAL FACTOR | FRUSTRATION INFLUENCE DEGREE Ie |
|---|---|
| TRAFFIC CONGESTION (SHORT) | 1 |
| TRAFFIC CONGESTION (MEDIUM) | 1.5 |
| TRAFFIC CONGESTION (LONG) | 2 |
| CUT-IN (HASTY) | 2 |
| CUT-IN (USUAL) | 1 |
| CUT-IN (EASY) | 0.5 |

*Fig.9*

|  | HR0 | HR1 | HR2 |
|---|---|---|---|
| BP0 | 0 | 0 | 1 |
| BP1 | 0 | 1 | 2 |
| BP2 | 1 | 2 | 2 |

*Fig.10*

|  | HR0 | HR1 | HR2 |
|---|---|---|---|
| BP0 | 0 | 0.5 | 1 |
| BP1 | 0.5 | 1 | 1.5 |
| BP2 | 1 | 1.5 | 2 | young # PSYCHOLOGICAL STATE ESTIMATION DEVICE

TECHNICAL FIELD

The present invention relates to a psychological state estimation device for estimating the psychological state of a subject, such as a frustration state or the like.

BACKGROUND ART

In order to improve safety during driving, various devices are suggested which estimate the psychological state of a driver, such as a frustration state or the like. As such an estimation device, for example, a device that is described in Patent Document 1 (JP-A-2006-34803) detects bioinformation, such as the heart rate or blood pressure of a subject, and judges a frustration state or the like on the basis of the magnitude relationship between the detected bioinformation and a prescribed threshold value. A device that is described in Patent Document 2 (JP-A-2003-61939) judges the frustration state or the like in consideration of the amount of road load by the vehicle speed or weather, as well as bioinformation. JP-A-2005-157662 and JP-A-2004-24879 also disclose a psychological state estimation device that estimates the psychological state of a subject.

DISCLOSURE OF THE INVENTION

When the frustration state is judged on the basis of the bioinformation, judgment is based on a prescribed numeric reference (threshold value), and accordingly the frustration state may be erroneously judged. For example, when the frustration state becomes high, the heart rate or blood pressure increases. For this reason, a heart rate or blood pressure higher than the normal state is set as a threshold value, and if the heart rate or blood pressure is equal to or more than the threshold value, it is judged that the frustration state is high. However, the heart rate or blood pressure may increase in other states, such as when the subject laughs loudly or the like, as well as when the frustration state is high. Accordingly, even if the frustration state is not high, it may be judged that the frustration state is high. As described above, the estimation accuracy of the frustration state is lowered when relying only on bioinformation.

When the frustration state is judged in consideration of the amount of road load (external environmental factor) as well as bioinformation, the frustration state may be erroneously judged as the individuals show different responses to such environmental factors. For example, when the drivers encounter a certain scale of traffic congestion, not all the drivers show the same degree of frustration state. While a driver who expected traffic congestion tends not to be in a high frustration state, another driver who has a hasty temper tends to be in a high frustration state. Accordingly, even if the drivers encounter the same environmental factor, actually, the influence on the frustration state varies according to the situations of the individuals. As described, above, even if bioinformation with an environmental factor is used, the estimation accuracy of the frustration state is lowered.

Accordingly, it is an object of the invention to provide a psychological state estimation device for estimating the psychological state of the subject with high accuracy.

A psychological state estimation device according to the invention for estimating the psychological state of a subject includes perception response acquiring means for acquiring the perception response of the subject to an external event, and estimating means for estimating the psychological state of the subject on the basis of the perception response acquired by the perception response acquiring means.

In this psychological state estimation device, the perception response acquiring means acquires the perception response of the subject who encounters an external event. Even if the subjects encounter the same external event, the subjects have different perception responses to the external event. A person who shows a strong response undergoes a strong influence on his/her psychological state, and another person who shows a weak response undergoes a weak influence on his/her psychological state. Accordingly, in the psychological state estimation device, the estimating means estimates the psychological state of the subject on the basis of the perception response. As described above, in this psychological state estimation device, the psychological states of the subjects are estimated in consideration of the perception responses of the individual subjects to the external event. Therefore, the influence of the external event on the psychological state can be exactly reflected in the individual subjects, and the psychological states of the subjects can be estimated with high accuracy. In this psychological state estimation device, the use of the perception response to the external event ensures instantaneous indication of the perception response to the external event as a response. Therefore, it is possible to cope with an instantaneous change in the psychological state of the subject.

The external event may be various external events (factors) that have an influence on the psychological state of the subject. For example, in the case of a driver, traffic congestion, cut-in, and road conditions may be exemplified. The perception response is a response to the subjects perception with respect to the external event when the subject encounters the external event. For example, there are an orienting response (a response to an accustomed external event, a weak response), a defensive response (a response cautious about an external event, a strong response), and no response (unconscious of an external event, lack of response). Examples of the psychological state include a frustration state, an impatient state, and a panic state.

The above-described psychological state estimation device of the invention may further include influence degree acquiring means for acquiring the degree of influence on a change in the psychological state of the subject on the basis of the perception response acquired by the perception response acquiring means. The estimating means may estimate the psychological state of the subject on the basis of the degree of influence acquired by the influence degree acquiring means.

In this psychological state estimation device, the influence degree acquiring means acquires the degree of influence on the change in the psychological state of the subject on the basis of the perception response to the external event. Then, in the psychological state estimation device, the estimating means estimates the psychological state of the subject on the basis of the degree of influence. As described above, in this psychological state estimation device, the degree of influence on the change in the psychological state is acquired on the basis of the perception response. Therefore, the influence of the external event on the change in the psychological state of each subject can be judged, and thus the psychological state of the subject can be estimated with high accuracy.

In the above-described psychological state estimation device of the invention, when the perception response acquiring means finds that the subject shows a defensive response, the influence degree acquiring means may increase the degree of influence on the change in the psychological state of the subject more than when the subject does not show the defensive response.

In this psychological state estimation device, when the perception response of the subject to the external event is a defensive response, the influence degree acquiring means increases the degree of influence on the change in the psychological state of the subject more than when the perception response is not a defensive response (an orienting response, no response, or the like). In the case of a defensive response, the subject is cautious about the external event, and thus the influence of the external event on the psychological state may be supposed to be strong. As described above, in this psychological state estimation device, in the case of a defensive response, the degree of influence on the change in the psychological state increases, and as a result, the psychological state of each subject can be estimated with high accuracy.

The above-described psychological state estimation device of the invention may further include bioinformation acquiring means for acquiring bioinformation of the subject. The estimating means may estimate the psychological state of the subject on the basis of the bioinformation acquired by the bioinformation acquiring means and the degree of influence acquired by the influence degree acquiring means.

In this psychological state estimation device, the bioinformation acquiring means acquires the bioinformation of the subject indicating the psychological state. Then, in the psychological state estimation device, the estimating means estimates the psychological state of the subject on the basis of the bioinformation indicating the psychological state and the degree of influence on the change in the psychological state by the perception response to the external event. As described above, in this psychological state estimation device, the psychological state of each subject is estimated in consideration of the bioinformation of each subject and the perception response of each subject to the external event, and as a result, the psychological state of each subject can be estimated with high accuracy. Bioinformation may be various kinds of information that can be biometrically measured from the human body when a person is in a psychological state. Examples of bioinformation include blood pressure, heart rate, and skin potential.

In the above-described psychological state estimation device of the invention, the influence degree acquiring means may set the degree of influence on the change in the psychological state depending on the external event and a perception response coefficient depending on the perception response acquired by the perception response acquiring means, and may acquire the degree of influence on the basis of the degree of influence on the change in the psychological state depending on the external event with the perception response coefficient.

In this psychological state estimation device, the influence degree acquiring means sets the degree of influence on the change in the psychological state of the external event itself and the perception response coefficient depending on the perception response of each subject to the external event, and acquires the final degree of influence on the basis of the degree of influence on the external event itself with the perception response coefficient. As described above, in this psychological state estimation device, the influence of the external event itself on the change in the psychological state and the influence on the change in the psychological state by the perception response of each subject to the external event are taken into consideration. Therefore, for each subject, the influence of the external event on the psychological state can be exactly reflected, and as a result, the psychological state of each subject can be estimated with higher accuracy.

BRIEF DESCRIPTION OF THE DRAWINGS

FIG. 6 shows an example of reference data of a frustration influence degree with respect to an environmental factor.

FIG. 9 shows an example of an evaluation table of frustration levels by bioinformation (heart rate and blood pressure).

FIG. 10 shows another example of an evaluation table of frustration levels by bioinformation (heart rate and blood pressure).

BEST MODE FOR CARRYING OUT THE INVENTION

Hereinafter, an embodiment of a psychological state estimation device according to the invention will be described with reference to the drawings.

In this embodiment, a psychological state estimation device according to the invention is applied to a frustration estimation device that is mounted on a vehicle to estimate the frustration level of a driver. In the frustration estimation device according to the invention, the frustration level of the driver is estimated in consideration of bioinformation indicating the frustration state of the driver with an environmental factor itself having an influence on the frustration state of the driver and a perception response to the environmental factor. Then, in the frustration estimation device according to the invention, the estimated frustration level is provided to various kinds of a driver support device, an alarm device, a frustration relaxation device, and the like.

Figure 1:
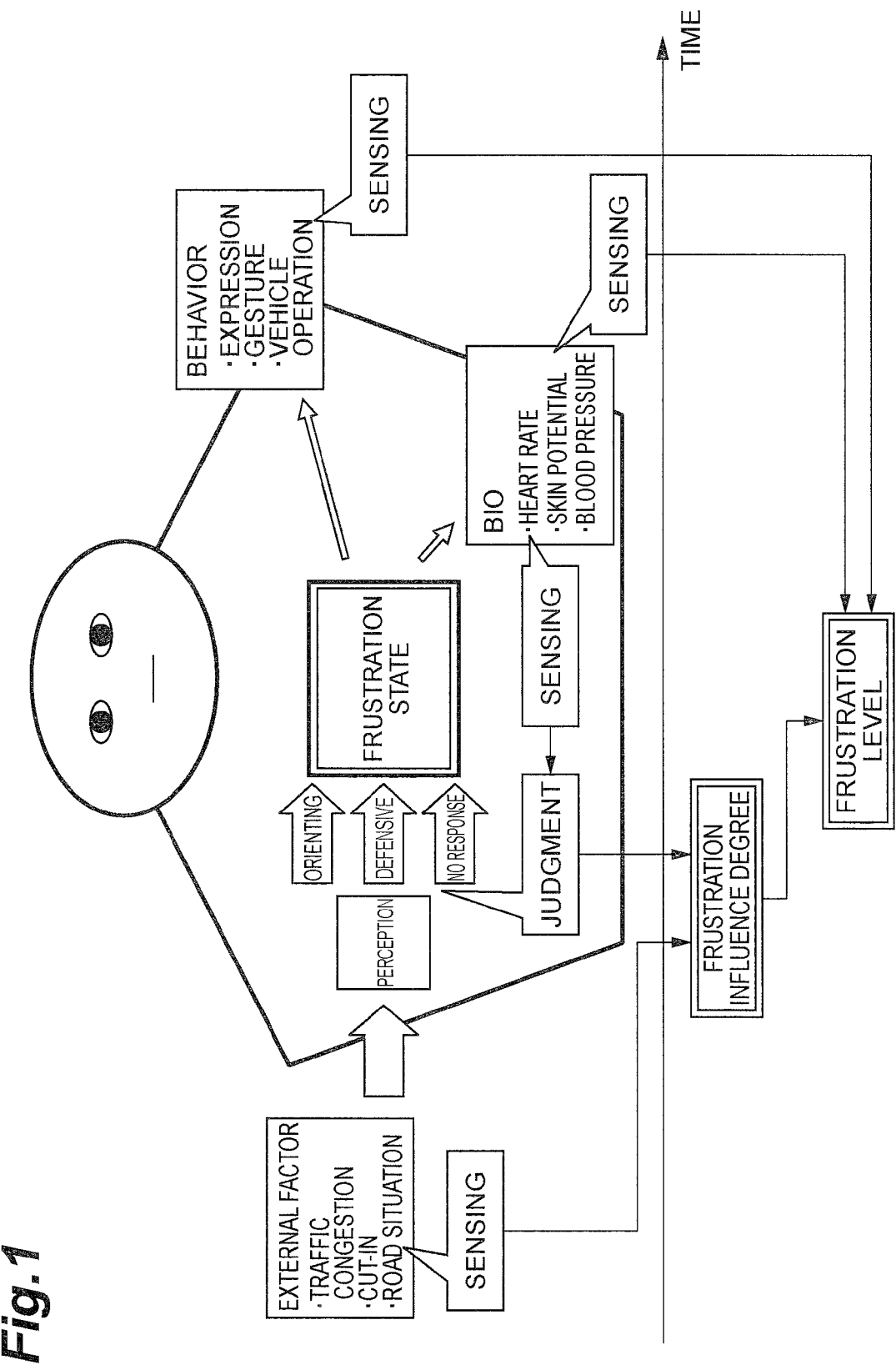
FIG. 1 is a conceptual view of this embodiment.

The overview of this embodiment will be described with reference to FIG. 1. FIG. 1 is a conceptual view of this embodiment. As an external environmental factor that is likely to make the frustration state of the driver high, traffic congestion, cut-in, and road conditions (winding road, narrow road, or the like) are sensed. When any one environmental factor is detected, bioinformation (skin potential and heart rate) of the driver is sensed, and the perception response (defensive response, orienting response, or no response) of the driver is judged on the basis of the bio response. When an environmental factor is detected, the frustration influence degree (reference value) for the environmental factor itself is set. Then, a final frustration influence degree is calculated on the basis of the frustration influence degree (reference value) with the perception response. In addition, bioinformation (heart rate and blood pressure) indicating the frustration state of the driver is sensed, and a frustration level (reference value) is set on the basis of the bio response. Then, the frustration influence degree is reflected in the frustration level (reference value) to estimate a final frustration level. Behavior information (expression, gesture, vehicle operation, or the like) of the driver other than bioinformation may be used.

When a person is stimulated by an environmental factor or the like, a perception response to the stimulus is instantaneously indicated by bioinformation or the like. For this reason, in the case of a perception response, as compared with a case where a frustration state is judged on the basis of bioinformation, a judgment interval can be significantly shortened and is in a second unit (in a minute unit when a frustration state is judged on the basis of bioinformation), and the type of bioinformation for judgment or the judgment criteria is different. In this embodiment, a skin potential response and a heart rate which easily produce an instantaneous response are used in order to judge a perception response.

A defensive response is a response cautious about a stimulus, a preparation step to the frustration state, and has a high response coefficient. An orienting response is a response to an accustomed stimulus, does not contribute much to the frustration state, and has a low response coefficient. No response is a state not conscious of a stimulus, has no influence on the frustration state, and has a response coefficient of zero.

In this embodiment, the frustration level to be estimated is a value ranging from 0 to 2, and it may be an integer value (0, 1, and 2), or not. The frustration level 0 means a usual calm state where frustration is not consciously felt. The frustration level 1 is a state where frustration is slightly consciously felt in a state of irritation. The frustration level 2 is an explosive state where frustration is significantly conscious and anger is suppressed. When the frustration level 2 is reached, an error in judgment, a sudden maneuver, or the like may easily occur during driving. For reference, a frustration level 3 means a state of explosive anger. The frustration level 3 may also be included in the estimation.

Figure 2:
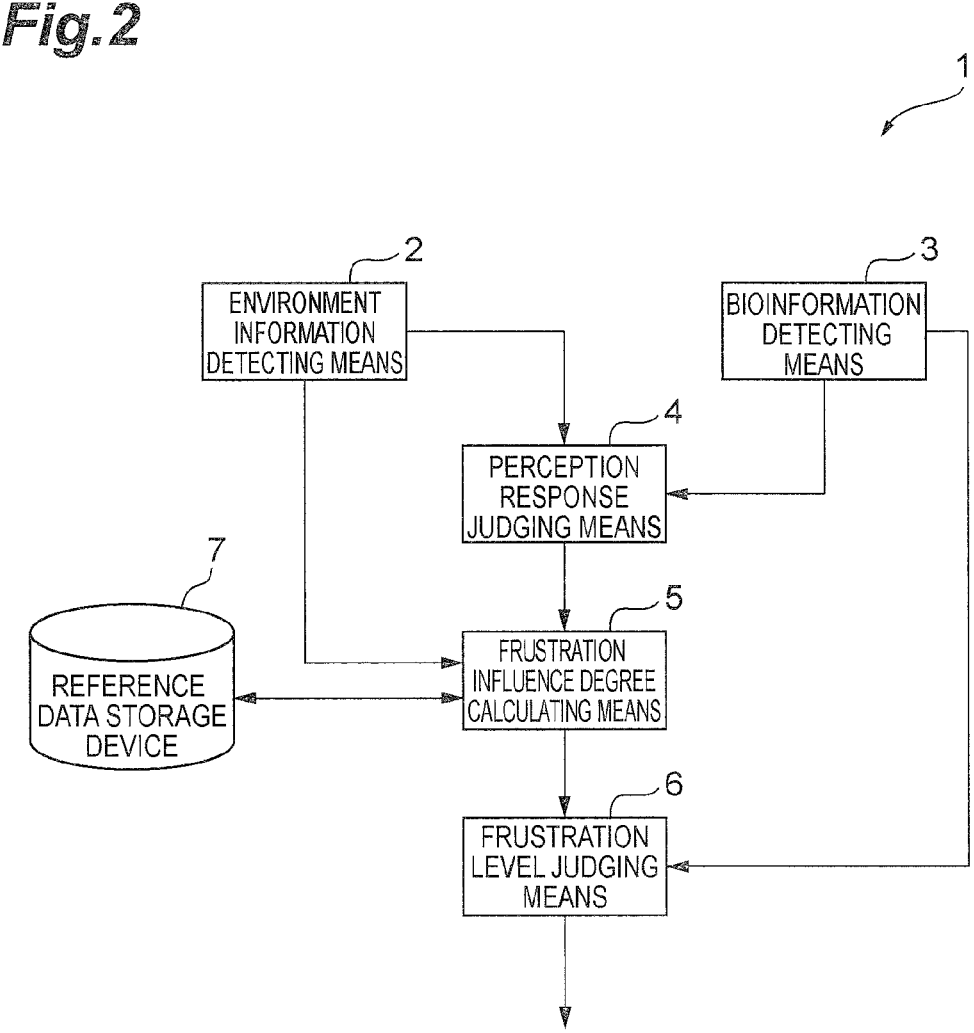
FIG. 2 is a block diagram of a frustration estimation device according to this embodiment.
Figure 3:
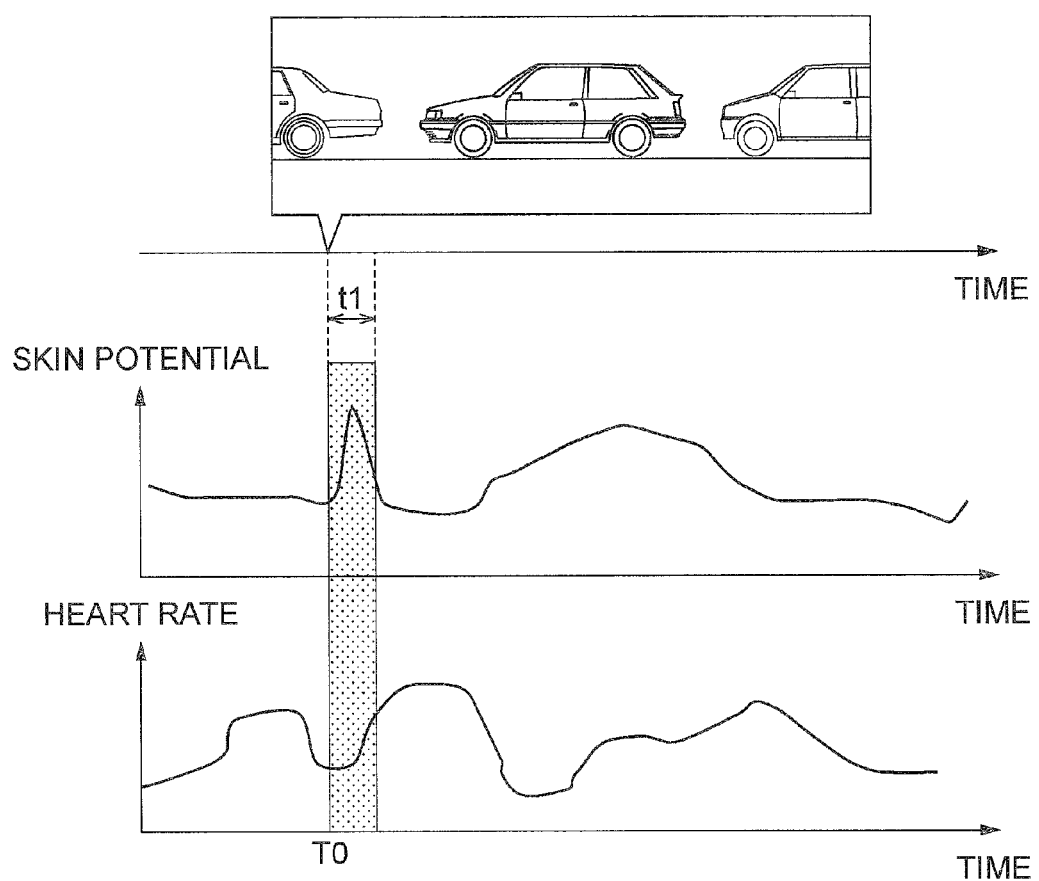
FIG. 3 shows an example of a temporal change in bioinformation (skin potential and heart rate) of a driver with respect to an environmental factor (traffic congestion).
Figure 4:
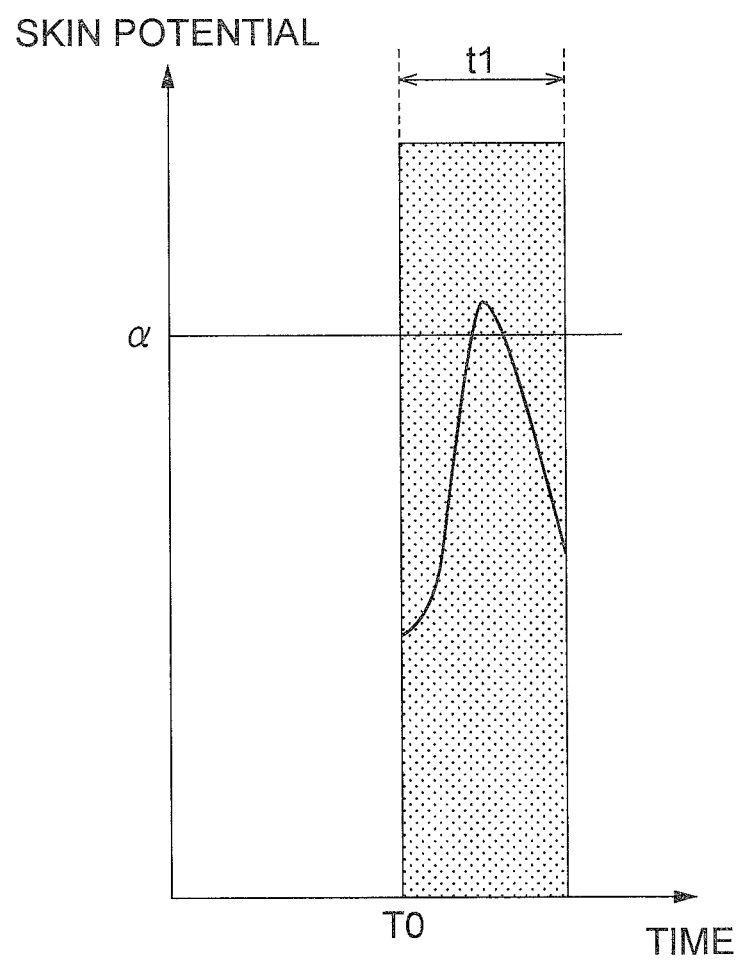
FIG. 4 shows an example of a temporal change in a judgment interval of the skin potential of a driver with respect to an environmental factor (traffic congestion).
Figure 5:
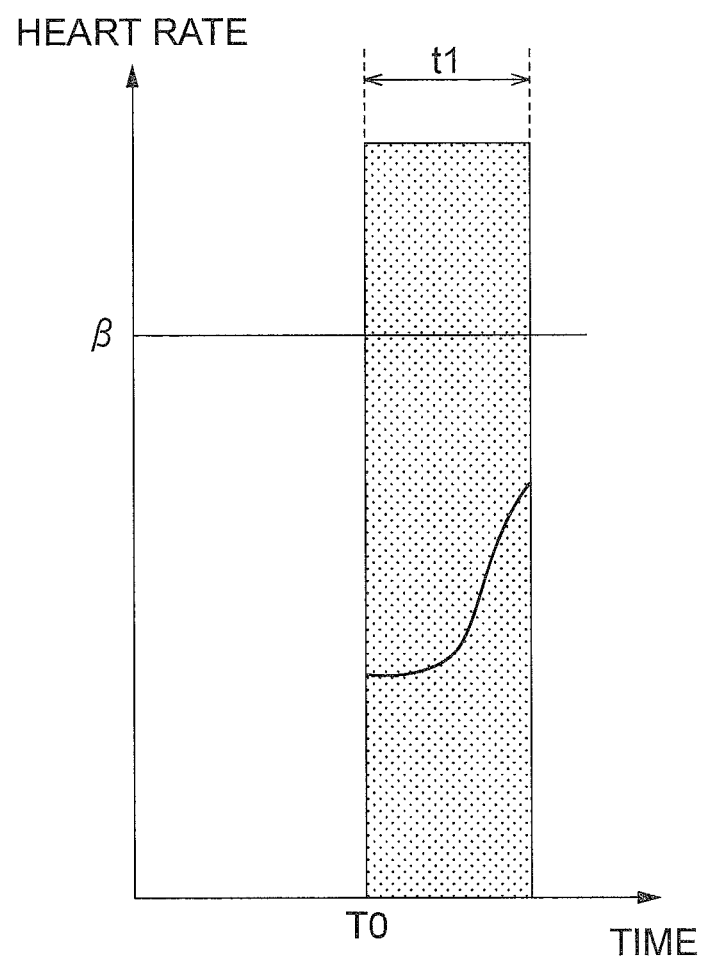
FIG. 5 shows an example of a temporal change in a judgment interval of the heart rate of a driver with respect to an environmental factor (traffic congestion).
Figure 7:
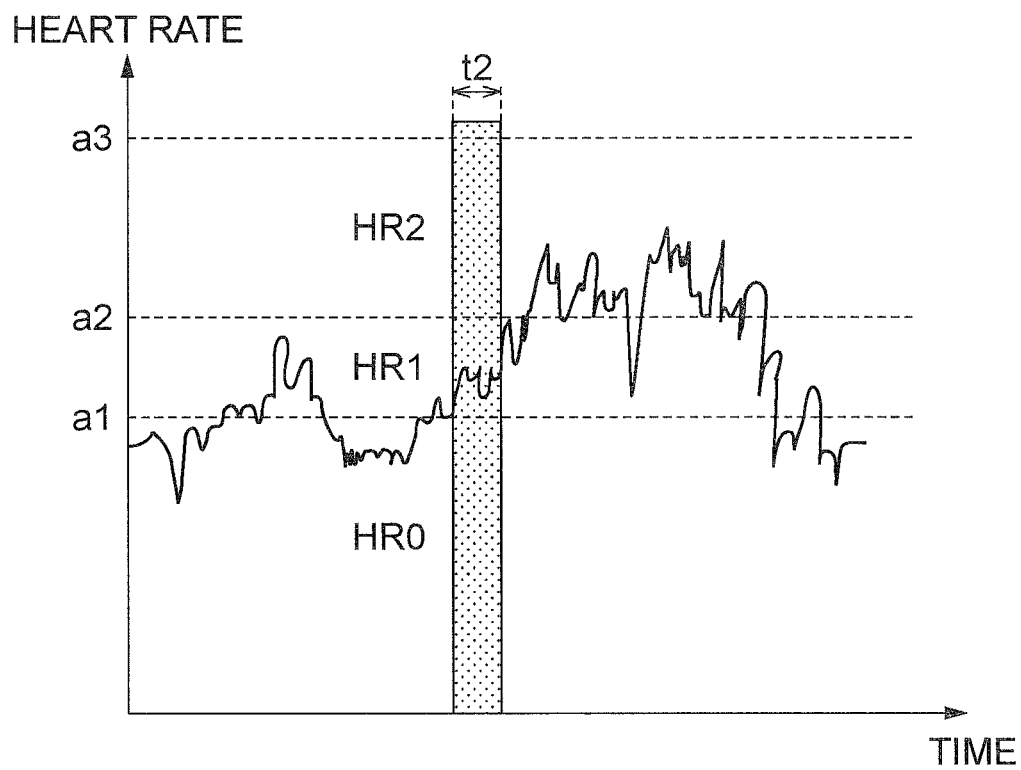
FIG. 7 shows an example of a temporal change in the heart rate of a driver.
Figure 8:
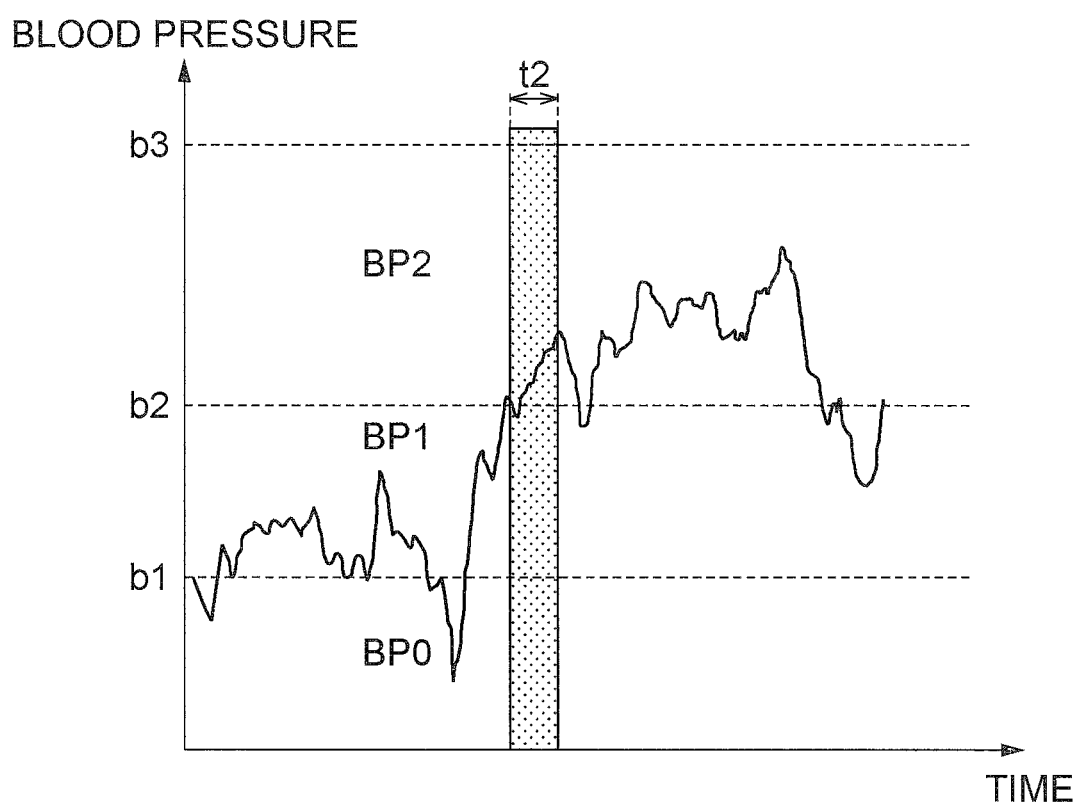
FIG. 8 shows an example of a temporal change in the blood pressure of a driver.
Figure 9:
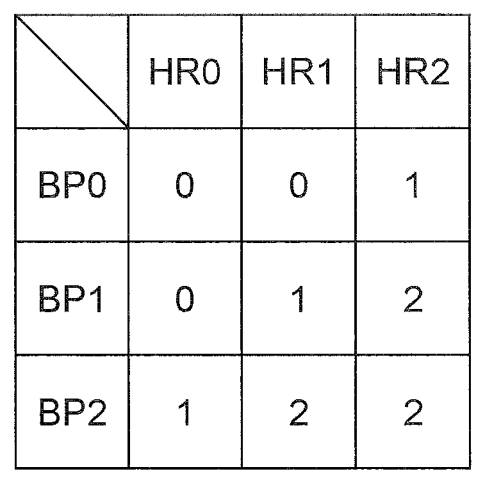
Figure 10:
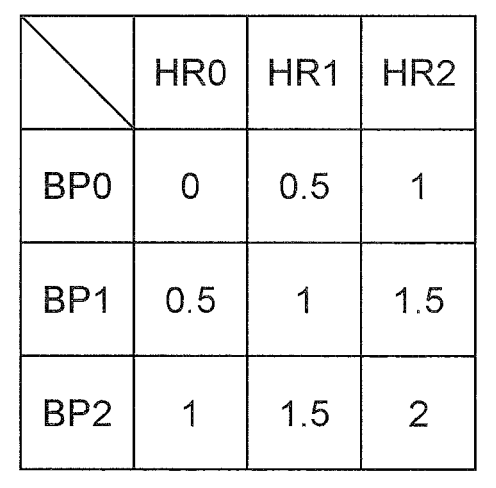

The frustration estimation device will be described with reference to FIGS. 2 to 10. FIG. 2 is a block diagram of a frustration estimation device according to this embodiment. FIG. 3 shows an example of a temporal change in bioinformation (skin potential and heart rate) of a driver with respect to an environmental factor (traffic congestion). FIG. 4 shows an example of a temporal change in a judgment interval of the skin potential of a driver with respect to an environmental factor (traffic congestion). FIG. 5 shows an example of a temporal change in a judgment interval of the heart rate of a driver with respect to an environmental factor (traffic congestion). FIG. 6 shows an example of reference data of a frustration influence degree to an environmental factor FIG. 7 shows an example of a temporal change in the heart rate of a driver. FIG. 8 shows an example of a temporal change in the blood pressure of a driver. FIG. 9 shows an example of an evaluation table of frustration levels by bioinformation (heart rate and blood pressure). FIG. 10 shows an example of an evaluation table of frustration levels by bioinformation (heart rate and blood pressure).

A frustration estimation device 1 estimates the frustration level on the basis of bioinformation indicating the frustration state and an external environmental factor that has an influence on the frustration state. In particular, in order to improve the estimation accuracy, the frustration estimation device 1 estimates the frustration level in consideration of the perception response of the driver to the environmental factor. To this end, the frustration estimation device 1 includes environment information detecting means 2, bioinformation detecting means 3, perception response judging means 4, frustration influence degree calculating means 5, frustration level judging means 6, and reference data storage device 7. The perception response judging means 4, the frustration influence degree calculating means 5, the frustration level judging means 6, and the reference data storage device 7 are formed by an ECU [Electronic Control Unit] of the frustration estimation device 1.

In this embodiment, the bioinformation detecting means 3 corresponds to bioinformation acquiring means described in the appended claims, the perception response judging means 4 corresponds to perception response acquiring means described in the appended claims, the frustration influence degree calculating means 5 corresponds to influence degree acquiring means described in the appended claims, and the frustration level judging means 6 corresponds to estimating means described in the appended claims.

The environment information detecting means 2 detects information on an environmental factor, such as traffic congestion or the like, which has an influence on the frustration state. For example, in the case of traffic congestion, a navigation device for acquiring VICS information (traffic congestion information or the like), a vehicle speed sensor for detecting a vehicle speed and a processor for judging traffic congestion on the basis of the vehicle speed, or a combination of them is used. In the case of cut-in, a vehicle speed sensor for detecting a vehicle speed and a processor for judging cut-in on the basis of the vehicle speed, a radar sensor for detecting an inter-vehicular distance and a processor for judging cut-in on the basis of the inter-vehicular distance, a camera for capturing a forward image and a processor for judging cut-in on the basis of image information, or a combination of them is used. In the case of road conditions, a navigation device having a map database, a camera for capturing a forward image and a processor for judging the road conditions on the basis of image information, or a combination of them is used. The individual processors of the environment information detecting means 2 may be formed in the ECU.

The bioinformation detecting means 3 detects, as bioinformation, skin potential (bioinformation electrically indicating mental sweating), heart rate, and blood pressure. Specifically, a skin potential sensor, a heart rate sensor (or an electrodiagram), and a blood pressure sensor are used.

When an environmental factor that has an influence on the frustration state of the driver is detected, the perception response judging means 4 judges the perception response of the driver to the environmental factor on the basis of the skin potential and the heart rate.

Specifically, the perception response judging means 4 judges whether or not the environment information detecting means 2 detects an environmental factor, such as traffic congestion or the like. When an environmental factor is detected, the perception response judging means 4 sets an interval t1, in which bioinformation for judgment of the perception response is to be extracted, with a time T0, at which the environmental factor is detected, as a start point. The interval t1 is a very short time range (in the order of seconds) for judgment of the perception response, and is set through an experiment or the like in advance. The perception response judging means 4 extracts a skin potential within the interval t1 starting with the time T0 from the skin potential detected by the bioinformation detecting means 3, and extracts a heart rate within the interval t1 starting with the time T0 from the heart rate detected by the bioinformation detecting means 3 (see FIG. 3).

The perception response judging means 4 judges whether or not the skin potential within the interval t1 is equal to or more than a reference potential α (see FIG. 4), and judges whether or not the heart rate within the interval t1 is equal to or more than a reference heart rate β (see FIG. 5). The reference potential α is a threshold value for judgment on whether or not the perception response to the environmental factor is indicated by the skin potential, and is set through an experiment for multiple drivers or the like in advance. The reference heart rate β is a threshold value for judgment on whether or not the perception response to the environmental factor is indicated by the heart rate, and is set through an experiment for multiple drivers or the like in advance. The reference potential α and the reference heart rate β have the same value for all the environmental factors, such as traffic congestion, cut-in, and the like.

The skin potential indicates mental sweating on the human body, and the value thereof instantaneously changes depending on the mental state (emotion or the like) of the human. For this reason, the skin potential instantaneously increases only when the driver perceives an environmental factor. Meanwhile, the value of the heart rate instantaneously changes when the human exercises or performs an action, such as becoming agitated or the like. Accordingly, when the driver perceives an environmental factor and takes any action, the heart rate instantaneously increases. When only the skin potential instantaneously increases significantly, it is supposed that the driver only perceives, and it is judged to be an orienting response. When the skin potential and the heart rate instantaneously significantly increase, it is supposed that the driver perceives and takes an action on the environmental factor, and it is judged to be a defensive response.

When the skin potential within the interval t1 is less than the reference potential α, the perception response judging means 4 sets the no response (0) as the perception response Res. When the skin potential within the interval t1 is equal to or more than the reference potential α and the heart rate within the interval t1 is less than the reference heart rate β, the perception response judging means 4 sets the orienting response (1) as the perception response Res. When the skin potential within the interval t1 is equal to or more than the reference potential α and the heart rate within the interval t1 is equal to or more than the reference heart rate β, the perception response judging means 4 sets the defensive response (2) as the perception response Res. For example, when the skin potential is equal to or more than the reference potential α, as shown in FIG. 4, and the heart rate is less than the reference heart rate β, as shown in FIG. 5, it is judged to be the orienting response.

Although judgment is made on the basis of the magnitude relation between bioinformation and the threshold value (the reference potential α and the reference heart rate β), other judgment methods may be used. For example, judgment may be made on the basis of a variation (differential value) in bioinformation within the interval t1 with respect to the threshold value, or judgment may be made on the basis of the degree of correlation with the reference waveform of bioinformation.

When an environmental factor that has an influence on the frustration state of the driver is detected, the frustration influence degree calculating means 5 calculates the frustration influence degree from the environmental factor itself and the perception response of the driver to the environmental factor. In this case, reference data that is stored in the reference data storage device 7 is used. Reference data is data in which a frustration influence degree (reference value) Ie is set for an environmental factor itself and is set through an experiment for multiple drivers or the like in advance. FIG. 6 shows an example of reference data. In the case of short traffic congestion, the frustration influence degree Ie is 1, in the case of medium traffic congestion, the frustration influence degree Ie is 1.5, and in the case of long traffic congestion, the frustration influence degree Ie is 2. In the case of hasty cut-in (for example, cut-in between vehicles with a short inter-vehicular distance), the frustration influence degree Ie is 2, in the case of usual cut-in, the frustration influence degree Ie is 1, and in the case of mild cut-in (for example, cut-in between vehicles with a sufficiently long inter-vehicular distance), the frustration influence degree Ie is 0.5.

Specifically, the frustration influence degree calculating means 5 refers to reference data of the reference data storage device 7, and extracts the frustration influence degree (reference value) Ie with respect to the detected environmental factor. For example, in the case of reference data shown in FIG. 6, when medium traffic congestion is detected, 1.5 is extracted as the frustration influence degree (reference value) Ie.

When the perception response Res is 0 (no response), the frustration influence degree calculating means 5 sets k0 as a perception response coefficient K. When the perception response Res is 1 (orienting response), k1 is set as the perception response coefficient K, and when the perception response Res is 2 (defensive response), k2 is set as the perception response coefficient K. The coefficients k0, k1, and k2 are values equal to or more than 0 and equal to or less than 1, and becomes higher as the perception response of the driver to the environmental factor becomes stronger (k0<k1<k2). For example, when k0=0, k1=0.3, and k2=1, in the examples of FIGS. 4 and 5, the orienting response is judged, and thus the perception response coefficient K becomes 0.3.

The frustration influence degree calculating means 5 multiplies the frustration influence degree (reference value) Ie by the perception response coefficient K, and sets the multiplication value as a final frustration influence degree (corrected value) If. For example, when the frustration influence degree (reference value) is 1.5 and the perception response coefficient K is 0.3, the frustration influence degree (corrected value) becomes 0.45.

The frustration level judging means 6 judges the final frustration level by reflecting the frustration influence degree in the frustration level (reference value) based on the heart rate and the blood pressure.

Specifically, the frustration level judging means 6 extracts a heart rate within an interval t2 from the heart rate detected by the bioinformation detecting means 3. The interval t2 is a time range (a time range longer than the interval t1, in the order of minutes) necessary for judgment of the frustration level from the bioinformation, and is set through an experiment or the like in advance. Then, the frustration level judging means 6 judges whether the heart rate of the interval t2 is less than a threshold value a1 (range HR0), equal to or more than the threshold value a1 and less than a threshold value a2 (range HR1), or equal to or more than the threshold value a2 and less than a threshold value a3 (range HR2) (see FIG. 7). The threshold values a1, a2, and a3 are values that are set through an experiment for multiple subjects or the Like in advance, and the conditional a1<a2<a3 is established. In the example of FIG. 7, the heart rate is judged to be in the range HR1.

The frustration level judging means 6 extracts a blood pressure within the interval t2 from the blood pressure detected by the bioinformation detecting means 3. Then, the frustration level judging means 6 judges whether the blood pressure within the interval t2 is less than a threshold value b1 (range BP0), equal to or more than the threshold value b1 and less than a threshold value b2 (range BP1), or equal to or more than the threshold value b2 and less than a threshold value b3 (range BP2) (see FIG. 8). The threshold values b1, b2, and b3 are set through an experiment for multiple subjects or the like in advance, and the condition b1<b2<b3 is established. In the example of FIG. 8, the blood pressure is judged to be in the range BP2.

The frustration level judging means 6 refers to an evaluation table and sets the frustration level (reference value) Ip corresponding to the judged heart rate range and the judged blood pressure range. The evaluation table is a table in which the frustration level (reference value) Ip is set for each combination of the heart rate ranges (HR0, HR1, and HR3) and the blood pressure ranges (BP0, BP1, and BP2), and is set through an experiment for multiple subjects or the like in advance. FIGS. 9 and 10 show an example of an evaluation table. In the example of FIG. 9, three frustration levels are set by integer values of 0, 1, and 2, and in the example of FIG. 10, five frustration levels of 0, 0.5, 1, 1.5, and 2 are set. In these examples, as the heart rate or blood pressure increases, the frustration level becomes high. When the heart rate is in the range HR1 and the blood pressure is in the range BP2, in the evaluation table of FIG. 9, the frustration level (reference value) Ip is 2, and in the evaluation table of FIG. 10, the frustration level (reference value) IP is 1.5.

The judgment method of the frustration level based on bioinformation is not limited to the above-described method, but various methods may be applied. For example, although a case where the number of classifications of bioinformation is 3 has been described, the number of classifications may be 2 or 4 or more. The variation within the interval may be judged with respect to the threshold value. Although the frustration level is set by the evaluation table, judgment may be made by using a predetermined judgment equation or the like.

The frustration level judging means 6 judges whether or not the frustration influence degree If is larger than 0. When the frustration influence degree If is 0 (the perception response is the no response), the environmental factor has no influence on the frustration state. For this reason, the frustration level judging means 6 sets the frustration level (reference value) Ip as the final frustration level I as it is. Meanwhile, when the frustration influence degree If is larger than 0 (the perception response is the orienting response or the defensive response), the environmental factor has an influence on the frustration state. For this reason, the frustration level judging means 6 calculates the final frustration level I by a frustration judgment equation F(Ip,If) in order to reflect the frustration influence degree If in the frustration level (reference value) Ip. With respect to the frustration judgment equation F(Ip,If), various formats of equations may be applied. For example, the equation F(Ip,If)=(a×Ip+b×If)/2 is used, where the coefficients a and b are set in advance and usually at 1.

When the frustration judgment equation F(Ip,If) is used, when the frustration level (reference value) Ip=2 and the frustration influence degree If=0.45 (when the driver encounters medium traffic congestion, but the perception response is the orienting response), the frustration level I=(1×2+1×0.45)/2=1.225 and becomes the frustration level 1. In this case, the driver encounters medium traffic congestion, but since this traffic congestion is the usual accustomed traffic congestion, the frustration state is judged to be light. For reference, when the frustration level is judged only on the basis of bioinformation, the frustration level (reference value) Ip=2 becomes the frustration level I as it is, and erroneous judgment may occur. In this case, while the frustration state is light with respect to medium traffic congestion, since the driver talks with a fellow passenger or listens to hard music, the heart rate or blood pressure increases. When the frustration level is judged on the basis of bioinformation and the environmental factor itself, the frustration influence degree (reference value) Ie=1.5, instead of the frustration influence degree If=0.45, is used, and the frustration level I=(1×2+1×1.5)/2=1.75 and becomes the frustration level 2. For this reason, judgment accuracy may be lowered. In this case, even if traffic congestion is accustomed and there is a low influence on the frustration state, since the influence on the frustration state is set by the medium traffic congestion itself, the frustration influence degree becomes higher than it actually was.

Figure 11:
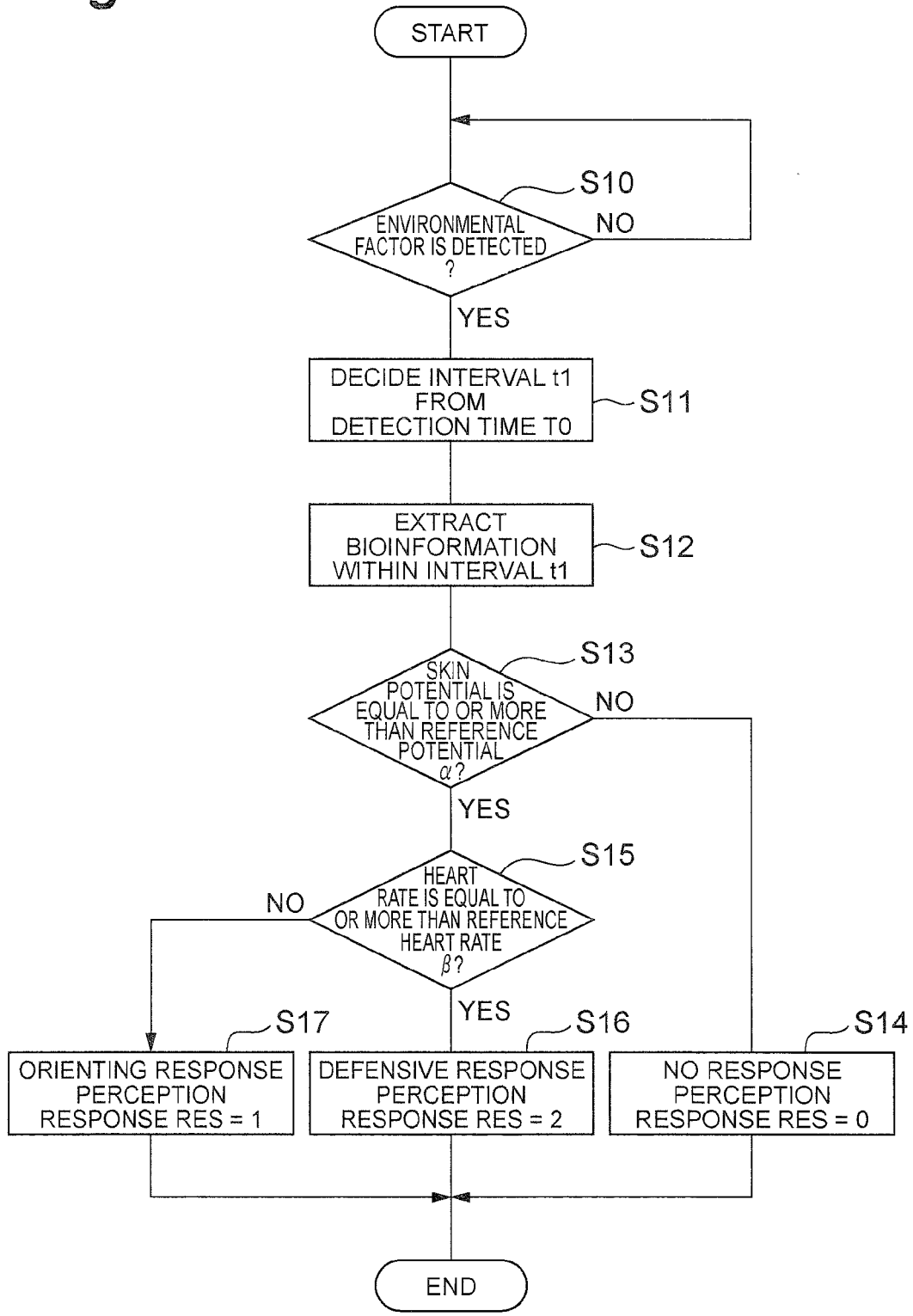
FIG. 11 is a flowchart showing the flow of a processing of perception response judging means shown in FIG. 2.
Figure 12:
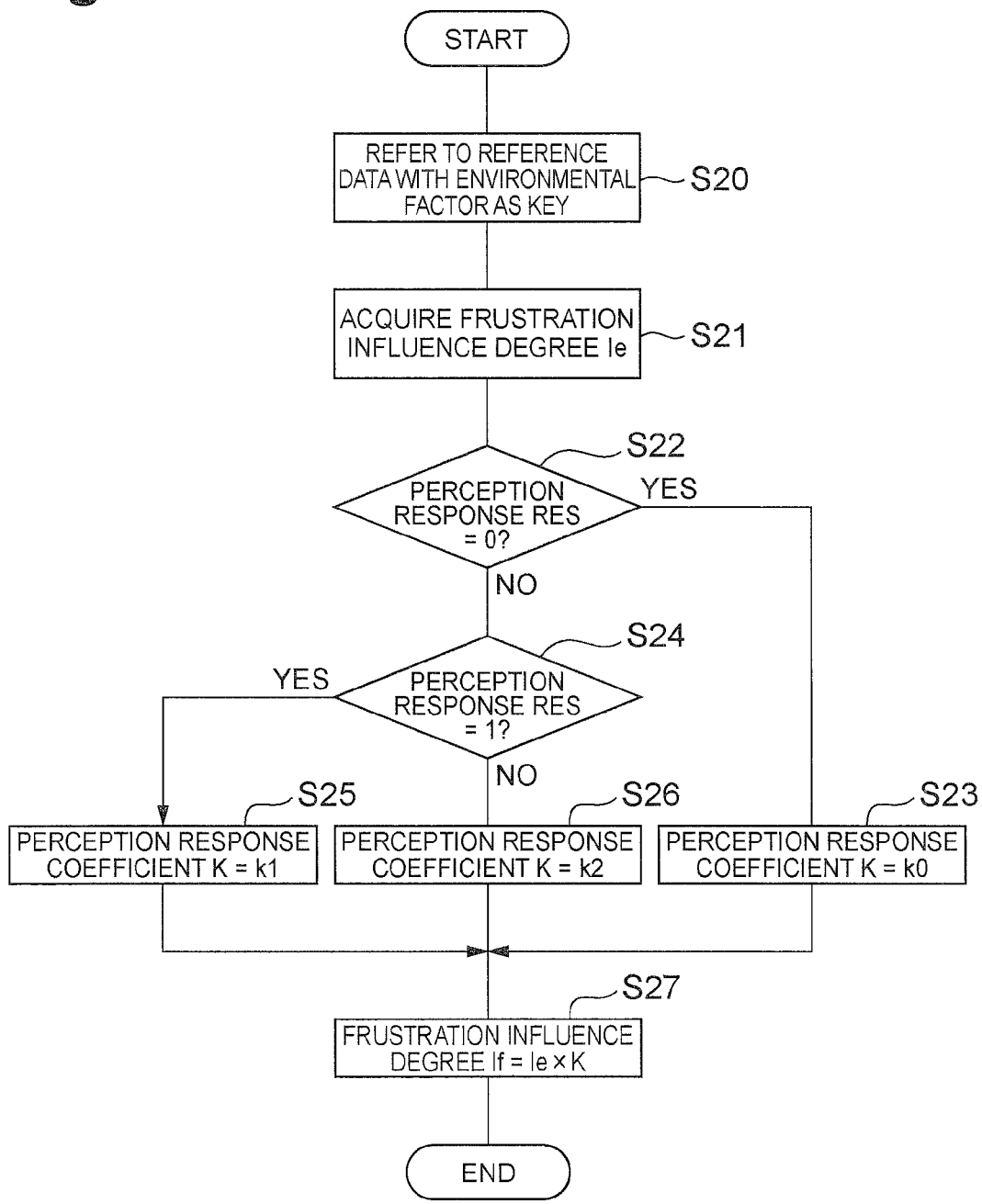
FIG. 12 is a flowchart showing the flow of a processing of frustration influence degree calculating means shown in FIG. 2.
Figure 13:
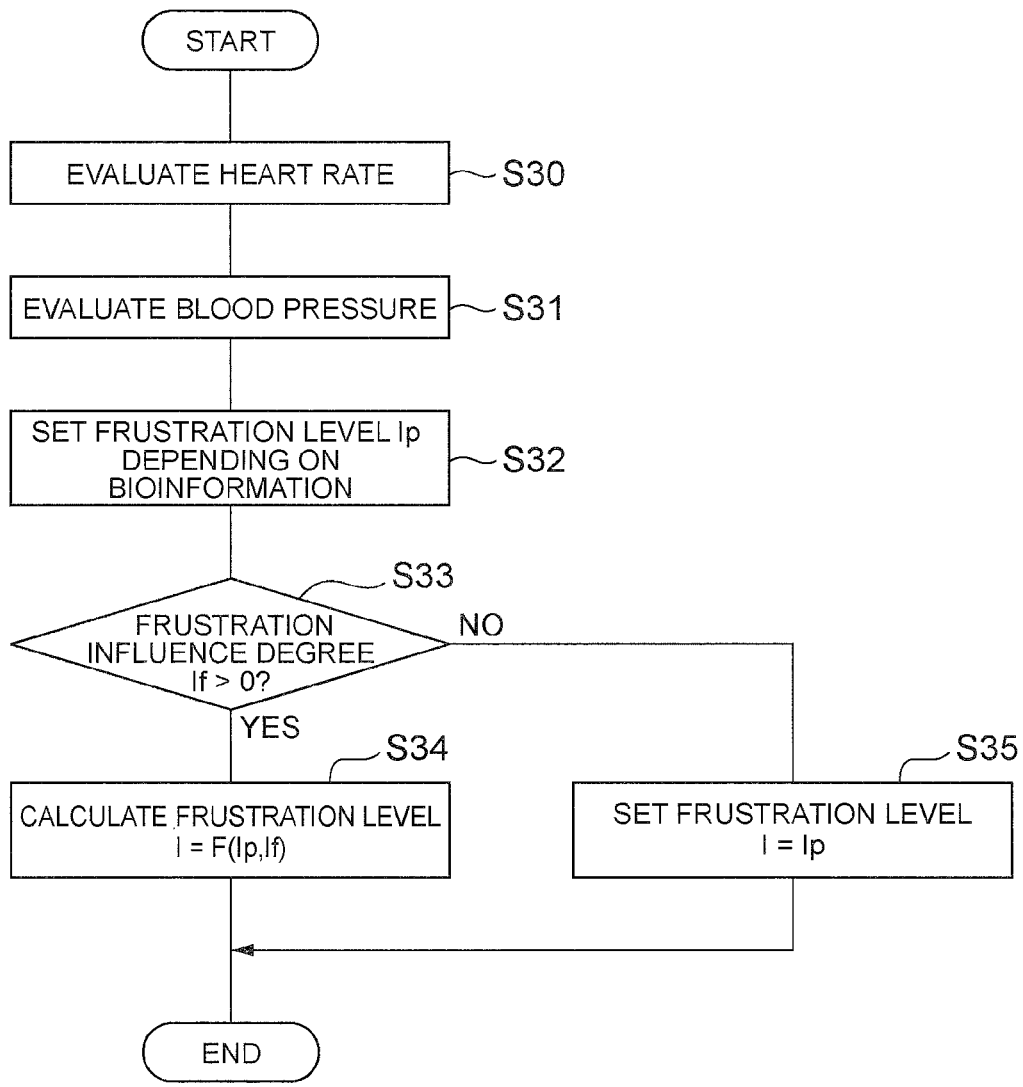
FIG. 13 is a flowchart showing the flow of a processing of frustration level judging means shown in FIG. 2.

The operation of the frustration estimation device 1 will be described with reference to the FIGS. 2 to 10. Specifically, a processing of the perception response judging means 4 will be described with reference to a flowchart of FIG. 11, a processing of the frustration influence degree calculating means 5 will be described with reference to a flowchart of FIG. 12, and a processing of the frustration level judging means 6 will be described with reference to a flowchart of FIG. 13. FIG. 11 is a flowchart showing the flow of a processing of the perception response judging means shown in FIG. 2. FIG. 12 is a flowchart showing the flow of a processing of the frustration influence degree calculating means shown in FIG. 2. FIG. 13 is a flowchart showing the flow of a processing of the frustration level judging means shown in FIG. 2.

The environment information detecting means 2 constantly senses an environmental factor, such as traffic congestion, cut-in, or the like. The bioinformation detecting means 3 constantly senses the skin potential, the heart rate, and the blood pressure.

The perception response judging means 4 judges at every predetermined time interval whether or not the environment information detecting means 2 detects an environmental factor, such as traffic congestion or the like (S10). When it is determined in S10 that an environmental factor is detected, the perception response judging means 4 decides the interval t1 starting with the detection time T0 (S11), and extracts a skin potential and a heart rate within the interval t1 from the skin potential and the heart rate detected by the bioinformation detecting means 3 (S12).

Then, the perception response judging means 4 judges whether or not the skin potential within the interval t1 is equal to or more than the reference potential α (S13). When it is determined in S13 that the skin potential within the interval t1 is less than the reference potential α, the perception response judging means 4 sets the no response (0) as the perception response Res (S14). Meanwhile, when it is determined in S13 that the skin potential within the interval t1 is equal to or more than the reference potential α, the perception response judging means 4 judges whether or not the heart rate within the interval t1 is equal to or more than the reference heart rate β (S15). When it is determined in S15 that the heart rate within the interval t1 is equal to or more than the reference heart rate β, the perception response judging means 4 sets the defensive response (2) as the perception response Res (S16). Meanwhile, when it is determined in S15 that the heart rate within the interval t1 is less than the reference heart rate β, the perception response judging means 4 sets the orienting response (1) as the perception response Res (S17).

Next, the frustration influence degree calculating means 5 refers to reference data of the reference data storage device 7 with the detected environmental factor as a key (S20), and acquires the frustration influence degree Ie for the detected environmental factor (S21).

Next, the frustration influence degree calculating means 5 judges whether or not the perception response Res=0 (no response) is satisfied (S22). When it is determined in S22 that the perception response Res=0 is satisfied, the frustration influence degree calculating means 5 sets k0 (=0) as the perception response coefficient K (S23). Meanwhile, when it is determined in S22 that the perception response Res=0 is not satisfied, the frustration influence degree calculating means 5 judges whether or not the perception response Res=1 (orienting response) is satisfied (S24). When it is determined in S24 that the perception response Res=1 is satisfied, the frustration influence degree calculating means 5 sets k1 (>k0) as the perception response coefficient K (S25). Meanwhile, when it is determined in S24 that the perception response Res=1 is not satisfied, the frustration influence degree calculating means 5 sets k2 (>k1) as the perception response coefficient K (S26).

Then, the frustration influence degree calculating means 5 multiplies the frustration influence degree Ie by the perception response coefficient K, and sets the multiplication value as the frustration influence degree If (S27).

The frustration level judging means 6 extracts a heart rate within the interval t2 from the heart rate detected by the bioinformation detecting means 3, and judges whether the heart rate within the interval t2 is less than the threshold value a1 (range HR0), equal to or more than the threshold value a1 and less than the threshold value a2 (range HR1), or equal to or more than the threshold value a2 and less than the threshold value a3 (range HR2) (S30). The frustration level judging means 6 extracts a blood pressure within the interval t2 from the blood pressure detected by the bioinformation detecting means 3, and judges whether the blood pressure within the interval t2 is less than the threshold value b1 (range BP0), equal to or more than the threshold value b1 and less than the threshold value b2 (range BP1), or equal to or more than the threshold value b2 and less than the threshold value b3 (range BP2) (S31). Then, the frustration level judging means 6 sets the frustration level Ip corresponding to the judged heart rate range and blood pressure range (S32).

Next, the frustration level judging means 6 judges whether or not the frustration influence degree If is larger than 0 (S33). When it is determined in S33 that the frustration influence degree If is larger than 0, the frustration level judging means 6 calculates the final frustration level I by the frustration judgment equation F(Ip,If) on the basis of the frustration level Ip and the frustration influence degree If (S34). Meanwhile, when it is determined in S33 that the frustration influence degree If is 0, the frustration level judging means 6 sets the frustration level Ip as the final frustration level I (S35).

Then, the frustration estimation device 1 outputs the estimated final frustration level I to various kinds of a driver support device, an alarm device, a frustration relaxation device, and the like.

According to this frustration estimation device 1, the frustration state is estimated in consideration of the perception response of each driver to the environmental factor which has an influence on the frustration state of the driver. Therefore, the influence of the environmental factor on the frustration state can be exactly reflected for each driver, and the frustration state of each driver can be estimated with high accuracy. In addition, the frustration estimation device 1 uses the perception response to the environmental factor. In this case, since the perception response indicates an instantaneous change in bioinformation, it is possible to cope with an instantaneous change in the frustration state. Therefore, in order to prevent instant perception or an error in judgment during driving (consequently, in order to prevent collision), the estimated frustration state can be used.

In the frustration estimation device 1, the perception response is judged in the three steps of no response, orienting response, and defensive response. Therefore, the influence of the environmental factor on the frustration state of each driver can be exactly judged, and the psychological state of each driver can be estimated with higher accuracy.

In the frustration estimation device 1, the frustration state of each driver can be estimated in consideration of the frustration level based on bioinformation of each driver with the perception response of each driver to the environmental factor. Therefore, the frustration state of each driver can be estimated with higher accuracy. In addition, in the frustration estimation device 1, since the degree of influence of the environmental factor itself on the frustration state and the influence of the perception response of each driver to the environmental factor are taken into consideration. Therefore, the influence of the environmental factor on the frustration state can be exactly reflected for each driver, and the psychological state of each driver can be estimated with higher accuracy.

Although the embodiment of the invention has been described, the invention is not limited to the foregoing embodiment, but it may be implemented in various ways.

For example, although in this embodiment, an application of the frustration estimation device that is mounted on a vehicle to estimate the frustration level of the driver has been described, the invention may be applied to devices for estimating other states, such as impatience, boredom, disillusion, panic, and the like, or may be applied to other objects, such as drivers of other vehicles, supervisors of various plants, night workers, or the like.

In this embodiment, the perception response is judged from the change in bioinformation depending on the environmental factor, the frustration influence degree (reference value) is set on the basis of the environmental factor itself, and the final frustration influence degree is calculated on the basis of the frustration influence degree (reference value) with the perception response. In addition, the final frustration level is calculated on the basis of the frustration level estimated from bioinformation with the frustration influence degree. Alternatively, the frustration level may be directly estimated on the basis of the perception response judged from the change in bioinformation depending on the environmental factor, without calculating the frustration level estimated from bioinformation, or the frustration level may be estimated on the basis of the perception response estimated from the change in bioinformation depending on the environmental factor and the environmental factor itself. Alternatively, the final frustration level may be estimated on the basis of the perception response estimated from the change in bioinformation depending on the environmental factor and the frustration level estimated from bioinformation.

Although in this embodiment, as the perception response, three responses of orienting response, defensive response, and no response are used, two responses may be used or four or more responses including additional responses may be used.

Although in this embodiment, as bioinformation for judgment of the perception response, the skin potential and the heart rate are used, and as bioinformation for judgment of the frustration level, the heart rate and the blood pressure are used, a single kind or three or more kinds of bioinformation may be used. Alternatively, other kinds of bioinformation may be used, or additional information, such as the behavior of the driver and the like, may be used.

INDUSTRIAL APPLICABILITY

With the psychological state estimation device according to the invention, the psychological state is estimated in consideration of the perception response of each subject to an external event, and as a result, the psychological state of the subject can be estimated with high accuracy.

The invention claimed is:

1. A psychological state estimation device for estimating the psychological state of a subject, comprising:
bioinformation acquiring means for acquiring skin potential, heart rate and blood pressure as bioinformation of the subject;
perception response acquiring means for acquiring a perception response, which is a response of a subject to a perception of an external event when receiving an external event having a possible impact on the psychological state of the subject, on the basis of the skin potential and heart rate;
influence degree acquiring means for acquiring the degree of influence on a change in the psychological state of the subject on the basis of the perception response acquired by the perception response acquiring means; and
estimating means for estimating the psychological state of the subject on the basis of the bioinformation acquired by the bioinformation acquiring means and the influence degree acquired by the influence degree acquiring means,
wherein the perception response acquiring means adopts a time at which the external event is received as a start point to set an interval in which bioinformation for determining the perception response is to be extracted, and with respect to the skin potential and heart rate, extracts a skin potential and heart rate, respectively, within the interval starting from the time, to set a no response as the perception response when the skin potential within the interval is less than a reference potential, to set an orienting response as the perception response when the skin potential within the interval is equal to or greater than the reference potential and the heart rate within the interval is less than a reference heart rate, and to set a defensive response as the perception response when the skin potential within the interval is equal to or greater than the reference potential and the heart rate within the interval is equal to or greater than the reference heart rate,
wherein the influence degree acquiring means sets the degree of influence on the change in the psychological state depending on the external event and a perception response coefficient depending on the perception response of either the no response, the orienting response or the defensive response acquired by the perception response acquiring means, and acquires the degree of influence on the basis of the degree of influence on the change in the psychological state depending on the external event with the perception response coefficient, and
wherein the estimating means:
refers to an evaluation table to set a frustration level corresponding to a heart rate range and a blood pressure range by extracting a heart rate of a preset interval from the heart rate to judge a value range of the heart rate of the interval on the basis of preset thresholds, and extracting a blood pressure of a preset interval from the blood pressure to judge a value range of the blood pressure of the interval on the basis of preset thresholds,
when the degree of influence is 0, sets the frustration level to a final frustration level, and
when the degree of influence is greater than 0, incorporates the degree of influence into the frustration level to calculate the final frustration level.

2. The psychological state estimation device according to claim 1,
wherein, when the perception response acquiring means finds that the subject shows a defensive response, the influence degree acquiring means increases the degree of influence on the change in the psychological state of the subject more than when the subject does not show the defensive response.

* * * * *